United States Patent [19]

Hildebrandt et al.

[11] 4,156,422
[45] May 29, 1979

[54] APPARATUS FOR TREATING HYDROCEPHALY

[75] Inventors: Jürgen J. Hildebrandt, Brunnthal; Wolfgang Plitz, Irschenhausen; Hans D. Herrmann, Bad Homburg, all of Fed. Rep. of Germany

[73] Assignee: Messerschmitt-Bolkow-Blohm GmbH, Munich, Fed. Rep. of Germany

[21] Appl. No.: 802,984

[22] Filed: Jun. 2, 1977

[30] Foreign Application Priority Data

Jun. 11, 1976 [DE] Fed. Rep. of Germany ....... 2626215

[51] Int. Cl.² .................. A61B 5/00; A61M 27/00
[52] U.S. Cl. .................. 128/748; 128/350 V
[58] Field of Search ............ 128/2 R, 1 R, 350 V, 128/350 R, 346

[56] References Cited

U.S. PATENT DOCUMENTS

| 3,527,226 | 9/1970 | Hakim | 128/350 V |
| 3,566,875 | 3/1971 | Stoehr | 128/350 V |
| 3,749,098 | 7/1973 | Bennetot | 128/346 |
| 3,757,770 | 9/1973 | Brayshaw et al. | 128/2 R |
| 3,924,635 | 12/1975 | Hakim | 128/350 V |
| 4,014,319 | 3/1977 | Favre | 128/2 R |

FOREIGN PATENT DOCUMENTS 401350 2/1974 U.S.S.R. .................. 128/2 R

Primary Examiner—Lee S. Cohen
Attorney, Agent, or Firm—W. G. Fasse; W. W. Roberts

[57] ABSTRACT

An apparatus for treating hydrocephaly has one housing which contains subcutaneously immplantable components for the measuring and controlling of fluid pressure. A second housing adapted to cooperate with the components in the first mentioned housing, contains the measuring and control components which remain outside a patient's skin. The components in both housings and the housings themselves are arranged for cooperation with each other, whereby an intracerebral space may be automatically drained in response to a predetermined, adjustable pressure.

14 Claims, 2 Drawing Figures

APPARATUS FOR TREATING HYDROCEPHALY

BACKGROUND OF THE INVENTION

The present invention relates to an apparatus for treating hydrocephaly, more specifically, for draining an intracerebral space in hydrocephalic patients. Such devices are capable of draining fluid from an intracerebral space by means of drainage conduits disposed subcutaneously and leading into a body cavity for the removal of fluid which has not been resorbed. Valve means are normally arranged in the drainage conduit.

Prior art drainage devices of the type described above are capable to remove fluid from a ventricular space when the fluid pressure in such space exceeds a predetermined valve pressure. Thus, such prior art devices are limited to preventing the continuous exceeding of a fluid pressure in the cerebral space which fluid pressure must be determined by separate measurements and by experience. This type of apparatus is further unable to prevent so-called hyper-drainage as a result of reduced pressure in the drainage conduit.

Furthermore, detailed investigations have shown that the fluid pressure in the ventricular space may differ in different patients and it may even differ in one and the same patient, depending on different circumstances, thus, the well being may be substantially disturbed in a patient who must use prior art drainage sytems in which the valve opening or response pressure is adjusted but once and thereafter cannot be changed again after implantation of the device.

OBJECTS OF THE INVENTION

In view of the above, it is the aim of the invention to achieve the following objects, singly or in combination:

to provide a drainage apparatus for the treatment of hydrocephaly which will perform the draining in a self-regulating manner, e.g. under the patient's control;

to provide a system for draining a ventricular space, wherein the pressure in such ventricular space is continuously adjustable in response to continuous medical observation of the patient;

to provide a drainage apparatus which will avoid even the temporary occurrence of reduced pressure and thus hyper-drainage, in response to reduced pressure occuring in the body cavity intended for receiving the drained fluid or in response to reduced static pressure in the drainage conduit itself;

to provide means which will enable the transcutaneous adjustment of the liquid pressure in a drainage apparatus as described herein;

to assure that the drainage will not be disturbed even if there may be a temporary gauge pressure in the body cavity intended to receive the drained fluid; and to construct all components intended for implantation in such a manner that optimal flow conditions are assured and that the settlement of pathogenic germs is avoided.

SUMMARY OF THE INVENTION

According to the invention, there is provided an apparatus for draining a cerebral cavity in a hydrocephalic patient, which apparatus includes in addition to the draining means, means for the transcutaneous measuring of the fluid pressure as well as means for the subcutaneous adjustment and maintaining of a predetermined pressure value. The means for maintaining the predetermined pressure preferrably comprise a proportional pressure control valve which is adjustable by an operator in a transcutaneous manner and which is controlled by the fluid pressure.

BRIEF FIGURE DESCRIPTION

In order that the invention may be clearly understood, it will now be described, by way of example, with reference to the accompanying drawings, wherein:

FIG. 1 is an axial section through an apparatus according to the invention, a portion of which is implanted between the head bone and the skin of a patient and a portion of the apparatus is located above the skin; and FIG. 2 is a sectional view of the pressure sensing and adjusting means as shown at A in FIG. 1, but on an enlarged scale.

DETAILED DESCRIPTION OF PREFERRED EXAMPLE EMBODIMENTS

Figure 1:
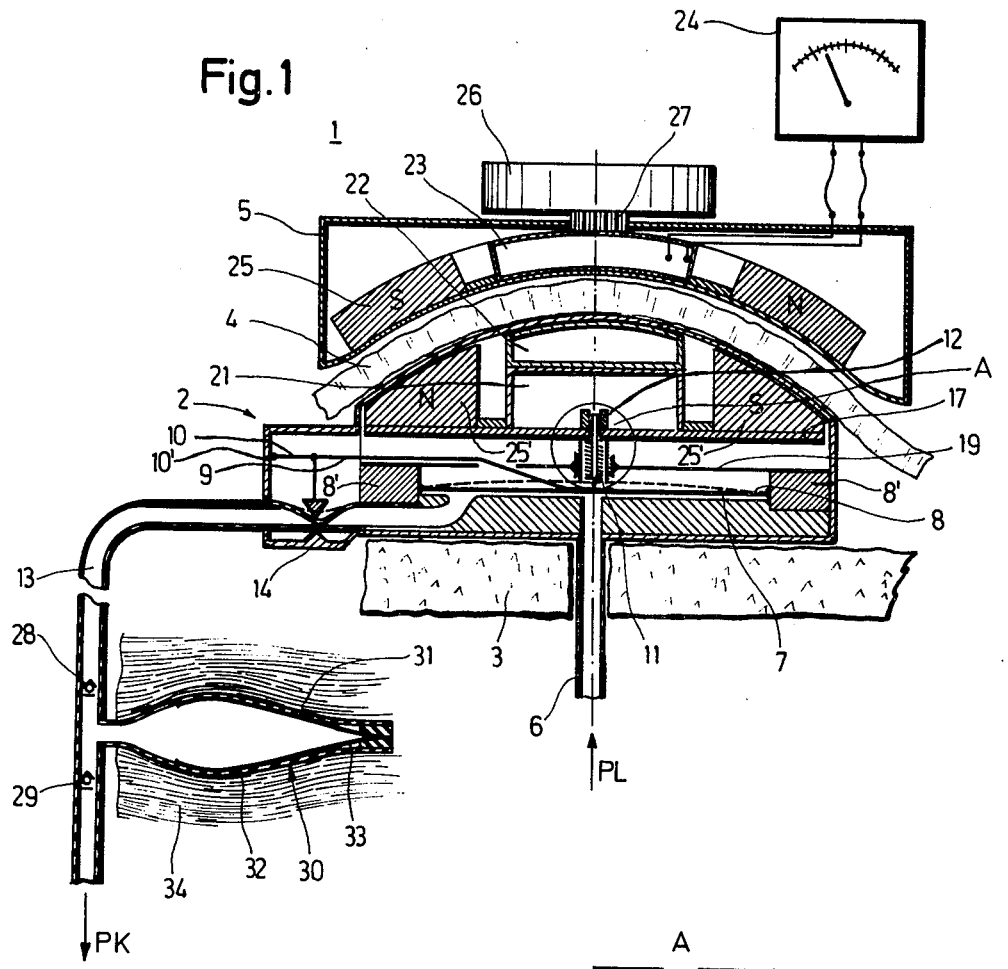

FIG. 1 shows the draining apparatus 1 according to the invention in an axial section. A first housing 2 is implanted between the head bone 3 and the head skin 4 of a patient. A second housing 5 contains components for the wireless measuring and adjustment of the pressure values as well as for the energy transmission into the unit contained in the housing 2. The fluid in a ventricular space is under the pressure "PL" as indicated by the arrow and enters into a relatively flat drainage chamber 7 through a first drainage conduit 6 in the form of a ventricular catheter which penetrates the head bone 3. The relatively flat drainage chamber 7 in the housing 2 is covered by a flexible diaphragm 8 held in position by frame members 8' in the housing 2.

Figure 2:
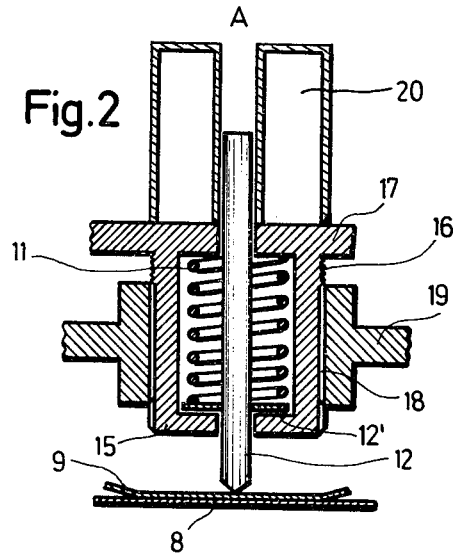

The diaphragm 8 will be bent upwardly under the fluid pressure entering the chamber 7 through the conduit 6. A lever arm 9 for controlling a proportional pressure control valve 14 contacts the diaphragm 8 as best seen in the enlargement of FIG. 2. The lever arm 9 extends into a further lever arm 10 which is pivoted to the housing 2 at 10'.

A pressure sensing pin 12, better seen in FIG. 2 contacts the diaphragm 8 and the lever arm 9 under the bias of a spring 11. The arrangement is such, that the valve 14 may be actuated through the levers arms 9, 10. The valve 14 is in the second conduit or discharge pipe 13 connected to the chamber 7. The conduit 13 connects to a body cavity of the patient, not shown. The lever arms 9 and 10 are arranged in a fixed ratio in accordance with the mean or average fluid pressure corresponding to the bias force of the spring 11 and with regard to the required force for adjusting the valve 14. Due to this ratio and due to the adjustment of the spring 11 a fluid pressure "PL" is established in the chamber 7 and thus in the ventricular space which is substantially dependent on the pressure exerted on the pressure sensing pin 12 by the spring 11 and thus by the pin 12 on the diaphragm 8.

In order to achieve the best possible results in the therapy of each individual patient, it is necessary to adjust the fluid pressure "PL" with due regard to the special circumstances of the individual patient. For this purpose, the bias of the spring 11 is adjustable at any time by an operator. The bias of the spring 11 is adjustable by means of the spindle 15 provided with a very fine threading 16 and forms the counter bearing for the pressure sensing pin 12. For this purpose, a disk 12' is rigidly secured to the pin 12. The spring 11 bears against the disk 12' and against a plate 17 to which the threaded spindle 15 is rigidly secured. Thus, the second bearing constituted by the adjustable spindle 15 may be rotated by magnetic means 25 and 25' through a knob 26. The magnetic means 25' are contained in the implanted housing 2 whereas the magnetic means 25 are contained in the housing 5. The threading 16 cooperates with a threading 18 in the support member 19 as best seen in FIG. 2. The support member 19 is secured to the housing 2 by the frame members 8'. By means of the just described elements, it is possible to rotate the magnetic plate 17 and thereby also the threaded spindle 15 in one or the other direction to thereby decrease or increase the bias force of the spring 11 onto the pressure sensing pin 12.

The axial displacement of the pressure sensing pin 12 is recorded by a displacement transducer 20 of well known construction whereby the pressure exerted by the pin 12 and thus by the spring 11 onto the diaphragm 8 may be ascertained. The axial movement of the pin 12 up and down in the transducer 20 provides an inductive signal which is connected to electronic amplifier means 21 and an oscillator which converts the received signals into signals which may be transmitted in a wireless, for example, inductive manner. The transmission of the measured signals as well as the energy supply of the electronic circuit means 21 is accomplished with the aid of alternating field transmitters and receivers 22, 23. Each of these units comprises a conventional transmitter and receiver. As previously mentioned, the receiver transmitter 23 is located in the housing 5 whereas the transmitter receiver 22 is part of the implanted unit in the housing 2. The housing 5 and the elements therein are shaped so as to conform to the outwardly bulging head skin 4 which in this area conforms to the shape of the housing wall portion of the housing 2 which covers the magnet 25' and the transmitter receiver means 22. An external indicator display device 24 is operatively connected to the transmitter receiver 23 whereby the fluid pressure "PL" may be directly indicated or displayed. Such fluid pressure indicators are also well known in the art.

The magnetic plate 17 and thus the bias of the spring 11 implanted in the housing 2 may be adjusted by means of the magnets 25 contained in the outer housing 5. The magnets 25 may be rotated continuously by a knob 26 or it may be rotated in steps by means of a ratchet mechanism 27. Such devices are also well known in the art. Depending on the position of the knob 26 either pulled or depressed, it is possible to engage or disengage the ratchet 27.

The discharge end 13 of the drainage conduit system is provided with at least one check valve 28, preferable is provided with two check valves 28, 29 as shown in FIG. 1. In order to increase the operational efficiency of the apparatus so far described, a pump 30 is connected to the discharge conduit 13 between the two check valves 28 and 29. These check valves prevent a back flow of fluid from the body cavity which receives the fluid, back into the cerebral space. The pump 30 assures a proper function of the apparatus even if the fluid pressure "PK" in the body cavity which receives the fluid, is higher than the fluid pressure "PL" in the ventricular space. As mentioned, the pump 30 is preferably connected to the conduit 13 between the valves 28 and 29. However, a connection upstream of the check valves would also be suitable.

The pump 30 may be of a known type comprising two flexible diaphragms 31 and 32 which may be spread by leaf spring members 33. The pump is implanted in muscle tissue 34 which is of the continuously operating or working type, for example, a muscle in the patient's breathing system. If the pump is in such a continuously operating position it produces an artifial pressure differential and the drainage outlet conduit 13 must be implanted accordingly with the check valves 28, 29.

In the light of the above disclosure, it will be appreciated that the present apparatus operates as follows. The pressure "PL" in the cerebral space enters through the catheter conduit 6 into the chamber 7 which is partially closed by the diaphragm 8 the biasing of which is adjustable through the knob 26 and by the elements previously described and especially illustrated in FIG. 2. Thus, a medical attendant is in a position to continuously adjust the pressure in accordance with the requirements of any particular patient, since he may now read the instantaneously prevailing pressure from the indicator 24. The diaphragm 8 simultaneously controls the lever arms 9 and 10 and through these lever arms the valve 14. The valve 14 in turn opens and closes the discharge conduit 13 in accordance with the instantaneous valve position. The arrangement of the valve is such that no sharp corners or fluid accumulating dead spaces are created. All the other components of the entire drainage system are also constructed to avoid sharp corners in the flow passage for the fluid to be drained. Similarly, any fluid accumulating dead spaces are minimized to avoid the settlement of pathogenic germs.

Further, by arranging the check valves in serial fashion upstream and downstream of the pump connection, a return flow is definitely prevented. Where a diaphragm pump is not employed, a single check valve will be sufficient for this purpose. However, where a diaphragm pump is used the arrangement of two check valves is preferable in order to provide a defined pressure drop in the discharge conduit. This feature of the invention has the advantage that even if there is a pressure in the cavity which receives the fluid, which is temporarily higher than the pressure in the ventricular space, fluid removal is still possible.

What is claimed is:

1. An apparatus for treating hydrocephaly by controlled draining of an intracerebral space into a body cavity, comprising draining means adapted for placement under the skin and for operatively interconnecting said intracerebral space and said body cavity, valve means operatively arranged in said draining means, fluid pressure measuring means operatively connected to said draining means for the transcutaneous measuring of the fluid pressure in said intracerebral space for providing a measured fluid pressure value, and transcutaneously adjustable pressure control means operatively connected to said valve means in said draining means for the transcutaneous adjusting and maintaining of a predetermined pressure value in said intracerebral space as a function of said transcutaneously measured fluid pressure value.

2. The apparatus of claim 1, wherein said pressure control means comprise proportional pressure control means operatively connected to said valve means, and adjustment means operatively connected to said proportional pressure control means, said adjustment means including subcutaneous components and external components for the transcutaneous adjusting of said subcutaneous components by said external components.

3. The apparatus of claim 2, wherein said draining means further comprise first conduit means, said adjustment means comprising chamber means, said first conduit means being adapted for operatively connecting said chamber means to said intracerebral space, diaphragm means forming one wall of said chamber means, transcutaneously adjustable spring means operatively arranged for biasing said diaphragm means into a position in which said diaphragm means normally close said first conduit means, lever means operatively interconnecting said diaphragm means and said proportional pressure control means, said lever means having a load arm connected to said proportional pressure control means and a force arm connected to said diaphragm means, said load arm and said force arm having a predetermined ratio, said draining means further comprising second conduit means operatively connecting said chamber means to said body cavity, said valve means being arranged in said second conduit means.

4. The apparatus of claim 3, wherein said adjustment means further comprise magnet means, threaded spindle means operable by said magnet means and operatively connected to one end of said spring means for adjusting the biasing force of said spring means, pin means operatively connected to the other end of said spring means, said pin means being connected in a force transmitting manner to said force arm engaging said diaphragm means.

5. The apparatus of claim 4, wherein said adjustment means further comprise a magnetic disk means operatively secured to said threaded spindle means.

6. The apparatus of claim 4, further comprising displacement transducer means operatively arranged to sense the displacement of said threaded spindle means, display means, and wireless transmission means operatively arranged between said transducer means and said display means for indicating the adjustment of said threaded spindle means.

7. The apparatus of claim 6, wherein said display means are calibrated in pressure units and wherein said transducer means comprise an inductive displacement transducer.

8. The apparatus of claim 6, wherein said wireless transmission means comprise alternating field receiver means adapted to be arranged subcutaneously and alternating field transmitter means arranged for transmitting energy to said alternating field receiver means in a transcutaneous manner.

9. The apparatus of claim 1, wherein said draining means comprise flow-off conduit means and check valve means operatively arranged in said flow-off conduit means downstream of said first mentioned valve means.

10. The apparatus of claim 1, wherein said draining means comprise flow-off conduit means and pump means, pump connection means operatively connecting said pump means to said flow-off conduit means, said apparatus further comprising check valve means including a first check valve arranged in said flow-off conduit means upstream of said pump connection means and a second check valve arranged in said flow-off conduit means downstream of said pump connection means.

11. The apparatus of claim 10, wherein said pump means comprise diaphragm pump means.

12. The apparatus of claim 11, wherein said diaphragm pump means are adapted for implantation in the body of a patient for actuation by muscle power.

13. The apparatus of claim 1, wherein said draining means comprise conduit means providing optimum flow conditions, said conduit means having at least on the inlet side upstream of said pressure control means uniform flow cross-sectional areas substantially along the entire length of said inlet side conduit means.

14. An apparatus for treating hydrocephaly by controlled draining of an intracerebral space into a body cavity, comprising draining means adapted for placement under the skin and for operatively interconnecting said intracerebral space and said body cavity, valve means operatively arranged in said draining means, fluid pressure measuring means operatively connected to said draining means for the transcutaneous measuring of the fluid pressure in said intracerebral space for providing a measured fluid pressure value, and transcutaneously adjustable pressure control means operatively connected to said valve means in said draining means for the transcutaneous adjusting and maintaining of a predetermined pressure value in said intracerebral space as a function of said transcutaneously measured fluid pressure value, wherein said fluid pressure measuring means comprise internal and external fluid pressure measuring components, wherein said transcutaneously adjustable pressure control means also comprise internal and external pressure control components, said apparatus further comprising first housing means containing said internal fluid pressure measuring components and said internal pressure control components, said first housing means being adapted for subcutaneous implantation, said first housing means comprising at least one wall with a predetermined shape, said apparatus further comprising second housing means containing said external fluid pressure measuring components and said external pressure control components, said second housing means also having at least one wall conforming to said predetermined shape to facilitate the transcutaneous cooperation of the respective internal and external components.

* * * * *